United States Patent
Arno (10) Patent No.: US 6,947,138 B2
(45) Date of Patent: Sep. 20, 2005

(54) OPTICAL SENSOR SYSTEM AND METHOD FOR DETECTION OF HYDRIDES AND ACID GASES

(75) Inventor: Jose I. Arno, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/462,526

(22) Filed: Jun. 16, 2003

(65) Prior Publication Data

US 2004/0252307 A1 Dec. 16, 2004

(51) Int. Cl.$^7$ .............................................. G01N 21/61
(52) U.S. Cl. ...................................... 356/347; 356/445
(58) Field of Search .............................. 356/337–439, 356/445–448

(56) References Cited

U.S. PATENT DOCUMENTS

| | | | | |
|---|---|---|---|---|
| 4,032,297 A | * | 6/1977 | Lyshkow | 422/91 |
| 4,367,736 A | * | 1/1983 | Gupton | 604/30 |
| 4,764,343 A | * | 8/1988 | Nyberg | 356/445 |
| 5,039,491 A | * | 8/1991 | Saaski et al. | 422/82.05 |
| 5,115,811 A | * | 5/1992 | Hartlaub et al. | 600/342 |
| 5,250,260 A | * | 10/1993 | Nakano et al. | 422/56 |
| 5,255,074 A | * | 10/1993 | Kimbell et al. | 356/445 |
| 5,319,975 A | * | 6/1994 | Pederson et al. | 73/335.01 |
| 5,341,214 A | * | 8/1994 | Wong | 356/437 |
| 5,727,498 A | * | 3/1998 | Hackler et al. | 116/206 |
| 6,096,557 A | * | 8/2000 | Tanaka et al. | 436/100 |
| 6,319,722 B1 | * | 11/2001 | Litwin et al. | 436/121 |
| 2003/0113931 A1 | * | 6/2003 | Pan et al. | 436/113 |

OTHER PUBLICATIONS

Said Al Mosheky, et al., "In Situ Real–Time Monitoring of a Fermentation Reaction Using a Fiber–Optic FT–IR Probe" Jun. 2001.

* cited by examiner

Primary Examiner—Richard A. Rosenberger
(74) Attorney, Agent, or Firm—Margaret Chappuis; Steven J. Hultquist; Yongzhi Yang (57) ABSTRACT

A gas sensor for detection of hydride and/or acid gas species, featuring a color changing material that changes color in exposure to hydride and/or acid gas species, component(s) for impinging radiation on the color changing material for reflection therefrom, and component(s) for receiving reflected radiation from the color changing material and responsively generating an output upon a change of color of the color changing material indicative of a presence of hydride and/or acid gas species in gas contacting the color changing material. The gas sensor may be embodied in a compact and efficient probe assembly, utilizing optical fibers to transmit incident radiation to the color changing material and to transmit reflected radiation to a detector and signal processing circuitry.

58 Claims, 4 Drawing Sheets

OPTICAL SENSOR SYSTEM AND METHOD FOR DETECTION OF HYDRIDES AND ACID GASES

BACKGROUND OF THE INVENTION

1. Field of the Invention

The present invention relates to an optical sensor system and method for detecting the presence of hydrides and acid gases, e.g., in semiconductor manufacturing process effluents and semiconductor manufacturing plant environments.

2. Description of the Related Art

In the manufacture of semiconductor products, hydrides and acid gases are frequently used, e.g., as etchants, source reagents, cleaning agents, reactants, chamber cleaning materials, process stream diluents, and treating agents for abatement of effluents of the semiconductor manufacturing plant.

In such applications, there is a need for corresponding monitoring equipment and techniques for detecting the presence of hydrides and acid gases in specific process streams, or gaseous environments of the semiconductor manufacturing facility, to ensure the absence of such gases where they pose a health or safety risk, or are required to be removed in the treatment of gaseous streams containing same.

An illustrative application of such type involves scrubbing of hydrides and acid gases from streams in which they are present, using dry scrubbing apparatus. The dry scrubber apparatus is typically arranged as a single-or multi-vessel installation, in which the scrubber vessel contains a dry scrubber composition such as a chemical sorbent material that irreversibly reacts with the hydrides and acid gases that are present in a gas stream flowed through the vessel.

Since such scrubbing consumes the active dry scrubber medium, it is desirable to monitor the gas discharged from the scrubber vessel. By such monitoring, the approach to "breakthrough" of the hydride and/or acid gas components from the vessel is sensed, and the vessel can be taken off-stream to enable change-out of the scrubber medium, whereby fresh dry scrubber material is provided for renewed on-stream processing of the hydride-and/or acid gas-containing stream.

The point at which the bed of dry scrubber material in the vessel becomes substantially exhausted by cumulative reaction with hydride and/or acid gas components in the gas stream is termed the "end point" of the scrubber material bed, and a corresponding sensor that is arranged to sense the end point is termed an "end point sensor."

Specific scrubber systems of such type can also include hydride and/or acid gas sensors that are disposed in the bed, e.g., at an intermediate portion thereof, or at scattered multiple sensing locations in the bed of dry scrubber material, to permit the progressive exhaustion of the scrubber material to be monitored, so that the need for change-out of the scrubber medium from the vessel can be more accurately scheduled during the active service life of the dry scrubber material, particularly in instances where the hydride and/or acid gas-containing stream is highly variable in concentrations of such gas stream components.

Conventional scrubber sensors, e.g., end point sensors, include two main categories of devices, electrochemical-based sensors and tape-based sensors.

Electrochemical sensors have two potential shortcomings in use. First, the analyte used to react with the gas stream has a tendency to dry out when used in applications where the gas stream being analyzed is of low relative humidity. Such low relative humidity conditions result in erratic measurements and ultimately sensor failure. Gas streams exhausted from semiconductor manufacturing tools and flowed to scrubbers are typically dry in character, making the use of electrochemical sensors problematic. Second, conventional electrochemical sensors are sometimes cross-sensitive to hydrogen gas ($H_2$), a significant disadvantage since hydrogen is frequently used as a reducing gas in semiconductor processes and correspondingly is present as a common component in gas streams being monitored for hydrides and acid gases.

Tape-based sensors also have inherent limitations when used for scrubber endpoint or general environmental safety monitoring. Such sensor units are characteristically expensive in the first instance, and their cost of ownership (COO) is substantial as a result of having to continually replace color-changing tapes. Such units have movable parts that require maintenance and sometimes result in failure. For example, sensor units of such type are equipped with a pump that draws up to 1 standard liter per minute (slpm) to the sensor tape, for contact therewith so that a color change of the tape indicates the presence of the target gas species. Tape-based sensors also employ electric motors for scrolling the tape after each sampled point. These and associated moving parts have lifetime and reliability issues.

Accordingly, it would be a substantial advance in the art to be able to monitor gas, e.g., a gaseous stream or a gaseous environment, for the presence of hydrides and acid gases, with a monitoring system and methodology that avoids the above-discussed deficiencies of conventional hydride and acid gas sensing technologies.

SUMMARY OF THE INVENTION

The present invention relates to an optical sensor system and method for detecting the presence of hydrides and acid gases, e.g., in semiconductor manufacturing process effluents and semiconductor manufacturing plant environments.

In one aspect, the invention relates to a gas sensor for detection of hydride and/or acid gas species, said gas sensor comprising:

(a) a sensor body;
(b) a sensing element mounted on the sensor body and arranged for contact with gas susceptible to presence of said hydride and/or acid gas species therein, said sensing element changing color in contact with gas containing said hydride and/or acid gas species;
(c) a source light optical fiber mounted in the sensor body to conduct source light to the sensing element;
(d) a detector optical fiber mounted in the sensor body to receive reflected source light from the sensing element;
(e) a light source coupled to the source light optical fiber for supplying source light thereto; and
(f) a detector coupled to the detector optical fiber and arranged to receive reflected source light from the detector optical fiber and to responsively produce an output indicative of presence or absence of hydride and/or acid gas species in gas contacted with said sensing element.

Another aspect of the invention relates to a gas sensor for detection of hydride and/or acid gas species, comprising a color changing material that changes color in exposure to hydride and/or acid gas species, means for impinging radiation on the color changing material for reflection therefrom, and means for receiving reflected radiation from the color changing material and responsively generating an output upon a change of color of the color changing material indicative of a presence of hydride and/or acid gas species in gas contacting the color changing material.

Yet another aspect of the invention relates to a method of detecting hydride and/or acid gas species in a gaseous medium latently susceptible to presence of same, said method comprising contacting the gaseous medium with a color changing material that changes color in exposure to the hydride and/or acid gas species, while impinging on the color changing material an incident radiation that is reflected from said color changing material, and monitoring the reflected radiation from the color changing material to detect a change of the reflected radiation indicative of a change of color of the color changing material due to presence of hydride and/or acid gas species in said gaseous medium, thereby detecting the hydride and/or acid gas species in the gaseous medium.

A still further aspect of the invention relates to a effluent treatment system arranged to receive a gaseous effluent from a process generating same, said effluent treatment system comprising an effluent treatment unit constructed and arranged to remove hydride and/or acid gas species from the gaseous effluent to produce a treated gaseous effluent having reduced content of hydride and/or acid gas species, and at least one gas sensor as described hereinabove, arranged for detection of hydride and/or acid gas species in the gaseous effluent.

As used herein, the term "hydride" means a compound of hydrogen with another, more electropositive element or group. Examples include boranes, arsine, phosphine, silane, etc. The term "acid gas" as used herein means a gas that in aqueous solution becomes a proton donor. Examples of acid gas species frequently encountered in semiconductor manufacturing effluents include $F_2$, HF, HCl, chlorine, $ClF_3$, $SiF_4$, $Br_2$, HBr, HI, $BF_3$, $BCl_3$, and $H_nSiCl_{(n-4)}$ (where n=1 to 3, inclusive).

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention is based on the discovery that optical sensing of colorimetric gas-indicating elements can be carried out in a manner that overcomes the deficiencies of prior approaches to hydride and acid gas monitoring. The gas monitoring system of the present invention can be readily fabricated and efficiently operated. It has no moving parts, and is not susceptible to variable humidity conditions, hydrogen cross-reactivity or hydrogen cross-sensitivity.

Figure 1:
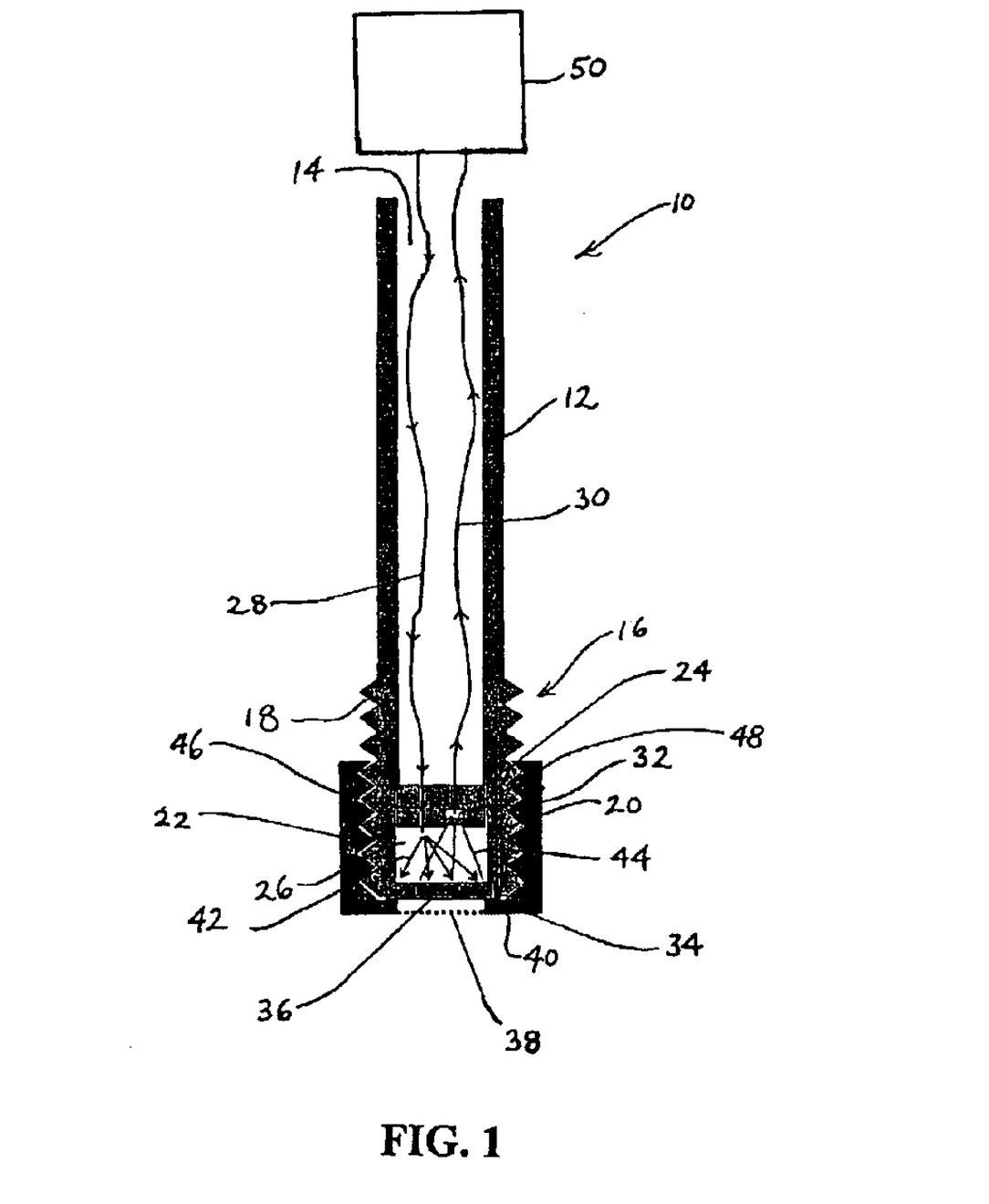
FIG. 1 is a schematic cross-sectional view of a gas-sensing probe, in accordance with one embodiment of the invention.

FIG. 1 is a schematic cross-sectional view of an optical gas-sensing probe 10, in accordance with one embodiment of the invention. The probe 10 includes a tubular probe body 12 defining a hollow tubular interior passage 14, and having a lower end 16 that is fabricated with threaded surface 18 for matable engagement with complementary threading 20 of the retaining cap 22 of the probe.

Directionally, the lower end 16 of the tubular probe body may be termed the "distal" end, with the upper open end of the tubular probe body correspondingly being termed the "proximal" end. The length of the tubular probe body, as measured along its longitudinal axis, may for example be on the order of from about 2 to about 100 cm in a specific embodiment, although it will be recognized that the size, shape and orientation of the tubular probe body as well as the gas sensor probe itself, may be widely varied in the general practice of the present invention, as regards specific applications and embodiments of the invention.

The retaining cap 22 is fabricated with an opening in its distal face 40. In this opening is disposed a protective mesh element 38. The function of the protective mesh element 38 is to permit ingress of gas from the bulk volume of gas being monitored for hydride(s) and/or acid gas(es), while occluding any deleterious particulates from entering the active sensing region of the probe. Alternatively, a gas-selective membrane can be substituted for or used in addition to the mesh in order to enhance the selectivity for the gas being analyzed. The bulk volume of gas may be a gaseous environment, e.g., in a room, or chamber, in which the gas sensing probe is disposed. Alternatively, the bulk volume of gas may be a flowing stream of gas, with which the gas sensing probe is contacted.

The active sensing region of the probe 10 comprises a distal portion 26 of the hollow tubular interior passage 14 that is forward of the fiber optics holder 24 and rearward of the optical window 34. A colorimetric (color-changing) element 36 is disposed on or in front of the optical window, and may comprise a sheet or web or other suitable article formed of a material that in the presence of the target gas species undergoes a calorimetric change. Examples of such colorimetric element 36 as useful for hydride gas detection include, without limitation: silver nitrate, copper hydroxide, copper carbonate, copper sulfate, mercury chloride, gold ($Au^{+3}$) complexes, and commercially available color-indicating dosimeters such as Gas Monitoring Dosimeter Type-1-Hydrides (GMD Systems, Inc., Pittsburgh, Pa.) and SAFEAIR® Arsine (K&M Environmental, Virginia Beach, Va.). For acid gas detection, a calorimetric matrix element containing iron oxide or acid/base indicators (such as methyl orange, bromocresol green, methyl red, bromocresol purple, bromothymol blue, and phenol red) can advantageously be employed.

The fiber optics holder 24 can comprise a cylindrical plug or disk element having a through-hole passage 46 therein, in which a source light optical fiber 28 is disposed with its end terminating at or in proximity to the distal face of the fiber optics holder. The fiber optics holder 24 also has a second through-hole passage 48 therein, in which a detector optical fiber 30 is disposed. The fiber optics holder 24 can be constructed as shown with a frontal cavity 32 in its distal face, with the detector optical fiber terminating at an end that is positioned at the floor of such frontal cavity or otherwise within the cavity.

Although the invention is illustratively shown and described with reference to embodiments including separate optical fibers for transmittal of source radiation and for transmittal of reflected radiation, it will be recognized that optical waveguide structures and elements of widely varying type may be employed in the general practice of the invention.

For example, the optical waveguide structure may comprise an optical fiber bundle in which source radiation and reflected radiation are transmitted by respective component fibers of the bundle, with all source radiation transmitting fibers being "pigtailed" to one side and coupled to a radiation source at the proximal end of the optical fiber array, and with all reflected radiation transmitting fibers being correspondingly pigtailed to another side and coupled to detector means at the proximal end of the optical fiber array.

Referring again to the embodiment illustratively depicted in FIG. 1, the source light optical fiber 28 and the detector optical fiber 30 extend readwardly from the fiber optics holder 24 to a source/detector module 50. The source/ detector module 50 is arranged to generate radiation of a specific character, e.g., a coherent light of a specific wavelength/frequency character. The generated radiation is supplied by the source/detector module 50 to the source light optical fiber 28, for transmittal along the fiber and discharge from the end face of the fiber in the distal portion 26 of the hollow tubular interior passage 14, as radiation 42.

The radiation 42 passes from the distal face of the fiber 28 and through the radiation-transmissive window 34 to the calorimetric element 36, from which it is reflected in the distal portion 26 of the hollow tubular interior passage 14 as reflected radiation 44. The reflected radiation 44 impinges on the distal end face of the detector optical fiber 30 in cavity 32, and is transmitted along the detector optical fiber to the source/detector module 50. The source/detector module 50 receives the reflected radiation from the detector fiber 30. In response to the character of the reflected radiation conducted to module 50 from the detector optical fiber 30, the module 50 generates an output indicative of the presence of the target gas (hydride and/or acid gas) species in the gas contacted with the color changing material 36, when the target gas species is present and produces a color change of the color changing material 36.

For such purpose, the module 50 may contain a detector, such as a photodiode, photoresistor, or other photosensitive or optoelectronic detector component, which is coupled to the proximal end of the detector optical fiber 30, and is operative to produce an output indicative of the presence of the target gas (hydride and/or acid gas) species in the gas contacted with the color-changing material 36.

For example, the source/detector module 50 can be arranged to submit the return radiation signal from the detector optical fiber 30 to signal processing operations in comparator circuitry in the source/detector module 50, against a signal based on the source light that is transmitted by the source light optical fiber 28 to the color-changing material 30.

It will be appreciated that the source/detector module 50 can be arranged in any of a wide variety of arrangements to provide a source light for supply to the source light optical fiber 28, and to receive the reflected light from the detector optical fiber 24, with appropriate circuitry, computational means (programmable general purpose computers, microprocessors, programmable logic controllers, registers, etc.), and the like, to generate an output indicative of the presence of the target gas species in the gas environment being monitored by the optical gas sensor. Such output may be indicative of mere presence of the target gas species in the monitored gas, or may be constituted to provide a quantitative indication of the concentration of the target gas species when present in the monitored gas contacted with the color-changing material of the sensor.

In one embodiment, the module 50 includes comparator circuitry that generates an output based on the source light and return reflected light characteristics. If the calorimetric element 36 in exposure to gas being monitored for the presence of the target gas species does not change color, thereby indicating the absence of the target gas species in the monitored gas environment, the comparator circuitry in the source/detector module 50 responsively outputs a null signal corresponding to such absence of the target gas species.

If, however, the colorimetric element 36 in exposure to gas being monitored for the presence of the target gas species changes color, thereby indicating the absence of the target gas species in the monitored gas environment, the comparator circuitry in the source/detector module 50 receives an altered reflected radiation signal from the detector optical fiber. The comparator circuitry then responsively outputs a positive signal corresponding to the presence of the target gas species. Such positive signal then can be passed to output, recording or alarm means indicative of such presence of the target gas species.

The radiation-transmissive window 34 may be formed of any suitable material of construction appropriate to the nature of the radiation that is being employed for the monitoring of gas for the presence or absence of the target gas species. For example, when the radiation is visible light, the radiation-transmissive window 34 can be formed of light-transmissive materials such as glass, quartz, fused silica, sapphire, etc. If the radiation is IR or UV radiation, correspondingly transmissive materials can be used, e.g., zinc selenide, zinc sulfide, sapphire, $CaF_2$, $MgF_2$, and other materials through which the radiation of the specific spectral character can pass for impingement on and reflection from the calorimetric element 34.

As used in such context, the term "calorimetric" is intended to be broadly construed as inclusive of changes that involve moderation or alteration of the incident radiation signal in a manner that is different when the element 34 has been exposed to the target gas species, in relation to the response of the element to incident radiation in the absence of exposure to the target gas species. Thus, the element 34 can be responsive to the presence of the target gas species by chemical reaction that alters the radiation absorbance or transmissivity of the material of the element, by adsorptive behavior (the element having a sorptive affinity for the target gas species, and the adsorbent-bearing element having different radiation-response characteristics than the element which has not been exposed to the target gas species).

The radiation-generating and radiation receiving elements in the source/detector module 50 can be of any suitable type. By way of example, the radiation generated by the module can, as mentioned, be in the visible, UV, or IR spectral regime, and can be generated by a radiation source such as a light-emitting diode, laser, or other source of the desired spectral character. The corresponding detector in the source/ detector module 50 can likewise be of any suitable type, e.g., a phototransistor or a photoresistor. The radiation source can be arranged to emit the generated radiation to a splitter, with a first part of the radiation being sent to the optical fiber 28 and a second part of the generated radiation being passed to an optoelectronic transducer or other means to generate a reference signal, e.g., for supply to comparator circuitry in the module 50.

The source/detector module 50 can be arranged with any other suitable signal processing circuitry, computational elements (gate elements, registers, microprocessors, etc.), and response output indicative of the presence of the target gas species in the gas environment being monitored. Such signal processing circuitry and other elements can be chip-based, as a unitary integrated circuit module, or may be constructed and arranged in any suitable manner, using any suitable means, for providing the capability of outputting a response when the probe 10 is exposed to the target gas species, and the colorimetric element 34 undergoes a responsive change that alters the radiation transmittance/ reflectance/absorbance characteristics of the color change element and produces an output indicative of the presence of the target gas species in the monitored gaseous medium.

The radiation-transmissive window 34 is preferably utilized to isolate the internal elements of the probe from the gas being monitored, so that the gas does not flow into the interior passage of the tubular member 12 and contaminate the probe and associated electronics. In some instances, the window can be eliminated from the probe assembly, e.g., where the target gas species is not toxic or hazardous, or where other control means are provided (e.g., a hydride or acid gas getter material is disposed in the interior passage of the tubular member 12) that render the window superfluous.

The window when employed can also be coated with an antireflective coating to prevent reflection of the radiation and enhance transmissivity of the window to the impinged radiation and radiation reflected from the colorimetric element.

In a preferred embodiment, the colorimetric element is capable of changing color when exposed to low concentrations (e.g., concentrations <1000 ppm, more preferably <100 ppm, and most preferably <10 ppm) of hydride gases (e.g., arsine, phosphine, silane, etc.) or acid gas species (e.g., hydrogen fluoride, hydrogen chloride, boron trifluoride, etc.). The colorimetric element can be formed of any suitable material, such as for example, impregnated paper, color-indicating polymer, granules of active (color-changing) materials, or a thin film directly coated on the optics window.

The protective mesh element 38 likewise can be of any suitable type, e.g., a screen, mesh, frit, sintered matrix, fibrous (woven or non-woven) web, or the like, which prevents particulate solids from impacting or interfering with the color change layer (calorimetric element), yet simultaneously allowing diffusion of gas to the calorimetric element to take place.

In operation, as the color of the calorimetric element changes in exposure of the element to hydride or acid gas, the reflected light changes in intensity, and is transferred through the detector optical fiber to the detector in the source/detector module 50. The change of the detected light can be processed as above described using comparator or other processing circuitry, and converted to a concentration reading, whose magnitude is determined by the extent of the change of the detected light. Alternatively, on exceeding a predetermined threshold, the change of detected light can be employed to generate a corresponding signal that incursion of the target gas species into the monitored gas environment has occurred. In another alternate embodiment, the detected light signal derivative with respect to time can be used to distinguish between a slow drift in response versus the fast light-to-dark transition that is characteristic of hazardous gas exposure.

Figure 4:
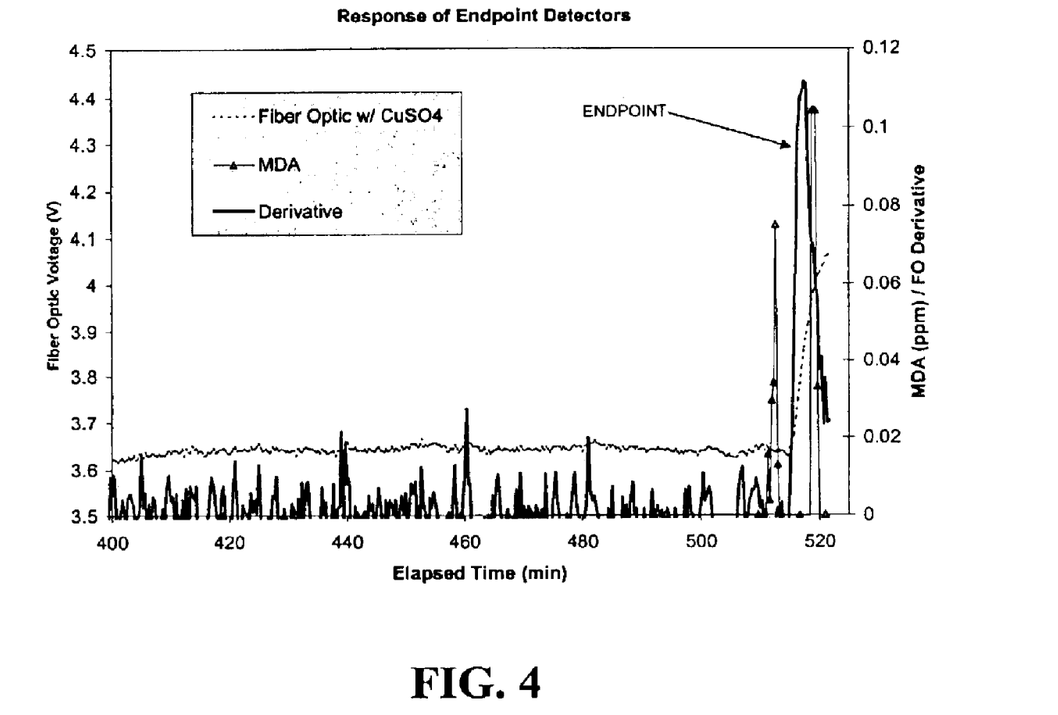
FIG. 4 is a graph depicting the response of a fiber optics sensor according to one embodiment of the present invention versus a commercially available TLD-1 Toxic Gas Detection System (Zellweger Analytics, Inc., Lincolnshire, Ill., USA) measuring the breakthrough of arsine gas from a dry scrubber.

FIG. 4. demonstrates the time-dependent response of a fiber-optics colorimetric system according to one embodiment of the present invention during a scrubber breakthrough experiment. Both the fiber optics probe constructed in accordance with the present invention and a TLD-1 Toxic Gas Detection System (commercially available from Zellweger Analytics, Inc., Lincolnshire, Ill., USA) were used to measure the exhaust gas stream discharged from a dry scrubber. The scrubber was challenged with a 2% arsine/$H_2$ gas mixture at a linear velocity of 2 cm/second. The fiber optic color-indicating element consisted of filter paper impregnated with copper sulfate. When arsine gas began to break through the scrubber bed (515 seconds into the test), the signal in the fiber optics device showed a marked increase coinciding with the TLD-1 Toxic Gas Detection System response. FIG. 4 depicts the direct voltage response in addition to the voltage gradient (derivative) of the signal. In this case, either curve could be used to detect gas breakthrough, although the derivative provides a more differentiated pattern. Inspection of the color-indicating element after completion of the test corroborated that the paper had changed from white to black.

Figure 2:
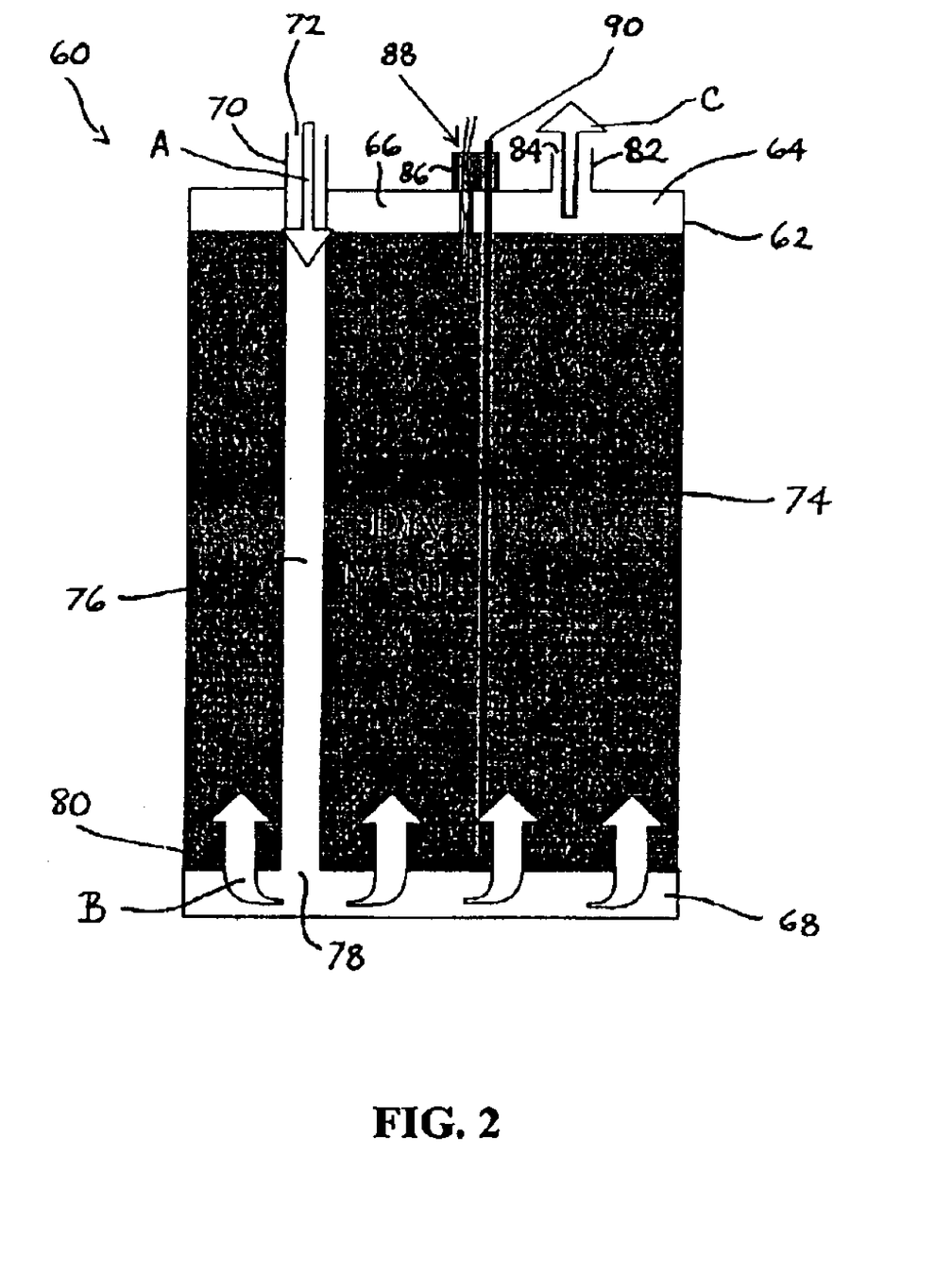
FIG. 2 is a schematic cross-sectional elevation view of an up flow scrubber unit featuring a gas-sensing probe according to another aspect of the invention.

FIG. 2 is a schematic cross-sectional elevation view of an up flow scrubber unit 60 featuring a gas-sensing probe 88 according to another aspect of the invention. The up flow scrubber unit 60 shown in FIG. 2 includes a vessel 62, which may be in the form of a canister, cylindrical container, or other housing, within which is disposed a bed of finely divided dry scrubber material ("Dry Media") 74.

The bed may be of any suitable dry scrubber material, such as metal oxide scrubber medium, or other suitable scrubber medium having abatement capability for the hydrides and acid gases in the effluent stream passed therethrough. Examples of scrubbing media suitable for the abatement of hydride gases include GV-5 (Matheson, Montgomeryville, Pa., USA), and NPT 170B (Sud-Chemie, Louisville, Ky., USA). Materials useful to scrub acid gases include 451D and S450 (ATMI, Inc., Danbury, Conn., USA). The bed of dry scrubber medium preferably comprises a chemisorbent material that irreversibly reacts with the hydrides and acid gases in the effluent stream to effect removal of such gases from the effluent stream.

The dry scrubber medium 74 can be in any suitable discontinuous form, such as in the form of pellets, spherical particles, monolithic forms, rings, or other regular or irregular shapes, and of suitable size to accommodate the operating characteristics of the unit. Such operating characteristics may be based on allowable pressure drop across the bed, associated blower/compressor requirements for effecting flow of the effluent stream, superficial velocity constraints required to avoid fluidization of bed material, etc. The operating characteristics and the corresponding scrubber design, bed sizing and vessel geometry are readily determinable within the skill of the art, for the provision of a scrubber unit of appropriate character for a specific effluent stream containing hydride and/or acid gas species.

The bed of dry scrubber medium 74 may be reposed in the vessel 62 on a support 80. The support can comprise a screen, mesh, grid or other suitable support structure accommodating passage of the effluent gas stream therethrough, for flow of the effluent gas through the bed of dry scrubber medium 74.

The bed of dry scrubber medium 74 is located in the vessel 62, with a lower plenum 68 located below the bed and an upper head space 64 located above the bed.

The vessel 62 is equipped with an effluent gas stream inlet 70 which can comprise a conduit having an open upper end 72, extending downwardly through the bed of dry scrubber medium 74, and terminating at an open lower end 78. By such arrangement, the effluent stream can be introduced into the open end 72 of the inlet conduit, in the direction indicated by arrow "A," for flow through the interior tubular passage 76 of the conduit to the open lower end 78 thereof, with discharge of the effluent gas into the lower plenum 68. From the lower plenum, the effluent stream is flowed upwardly through the bed of dry scrubber medium 74, in the direction indicated by arrows "B."

The effluent stream in passing upwardly through the bed of dry scrubber medium 74 is contacted with the scrubber medium particles in the bed, thereby effecting removal of hydrides and acid gases from the effluent stream. The hydride-and acid gas-reduced effluent stream then passes from the upper end of the bed of dry scrubber medium 74 into the upper head space 64 and is discharged from vessel 62 in outlet 82 through open discharge end 84 thereof. The discharged gas, reduced in content of hydrides and acid gases, flows from the outlet in the direction indicated by arrow "C" and may be subjected to further treatment, recycled to an upstream process unit, or released to the atmosphere, as appropriate.

The up flow scrubber unit 60 is equipped with a gas-sensing probe 88 that can be constructed as shown and described with reference to FIG. 1 hereof. The probe 88 is fixtured in a mounting block 86 through which a tubular body containing the optical fibers extends to a distal end where the optical fibers are coupled to the sensing head of the probe. The mounting block 86 also has a temperature sensor 90 fixtured therein. The temperature sensor 90 may be arranged to sense temperature at various points along the length of the bed (in the vertical direction, as shown in the orientation of FIG. 2). For example, the temperature sensor may comprise thermocouples that are spaced apart at regular or otherwise predetermined intervals along the length of the bed, to measure temperature change incident to exothermic (or endothermic) abatement reactions taking place when the effluent stream is contacted with the dry scrubber medium in the bed.

The optical fiber leads (source light optical fiber and detector optical fiber) extending upwardly from the mounting block 86 can, as shown in FIG. 1, be coupled to a suitable control module, comprising a light source and detection capability. The temperature sensor 90 likewise may have associated leads or signal transmission lines (not shown in FIG. 2) that are coupled with such control module to provide further monitoring or adjustment capability.

For example, the temperature sensor may be arranged to monitor temperature at discrete locations along the height of the bed, so that in the case of exothermic abatement reactions in the bed, any hot spots are detected and corrective action taken to avoid excessive heating problems, e.g., a control signal indicative of the excessive heating may be transmitted to a flow control valve in the effluent stream supply line, so that the flow rate of effluent gas to the scrubber unit is reduced, to reduce bed temperature in the scrubber to an appropriate level. Other monitoring and control arrangements can be implemented using a temperature sensor of the type shown in FIG. 2, to enhance operability and efficiency of the scrubber unit.

In operation, the gas-sensing probe 88 senses the presence of hydride and/or acid gas species at the lower end (sensing head) of the probe, to determine when such contaminant species have "broken through" at the sensor location in the bed. For example, the probe may be disposed with its sensing head in the exit end portion of the bed, at a point that is 90% of the length of the bed, as measured from its lower face (or alternatively stated, the sensing head of the probe may be positioned at a 10% depth into the bed as measured from its upper exit face), whereby 90% breakthrough of acid gas and/or hydride components can be sensed, indicating that only 10% of bed capacity remains.

In this manner, the probe is appropriately arranged to sense the approach of bed exhaustion (consumption of the dry scrubber medium), and the corresponding need to change-out the dry scrubber medium, e.g., by replacing the canister unit containing the spent dry scrubber medium, and/or switching of the effluent stream to a second vessel containing fresh scrubber medium.

It will be recognized that the optical sensor probe 88 may have a sensing head that is disposed at any suitable height within the bed, as appropriate to the monitoring of the scrubbing operation and the correlative action of determining the progress of the scrubber unit toward exhaustion of the dry scrubber medium, so that change-out of the scrubber medium or canister comprising same is done in a timely fashion.

Further, multiple probes may be employed, each having an associated sensing head disposed at a different position in the scrubber bed, along the direction of gas flow therethrough, to provide a fully monitored capability for the scrubbing and change-out operations.

Figure 3:
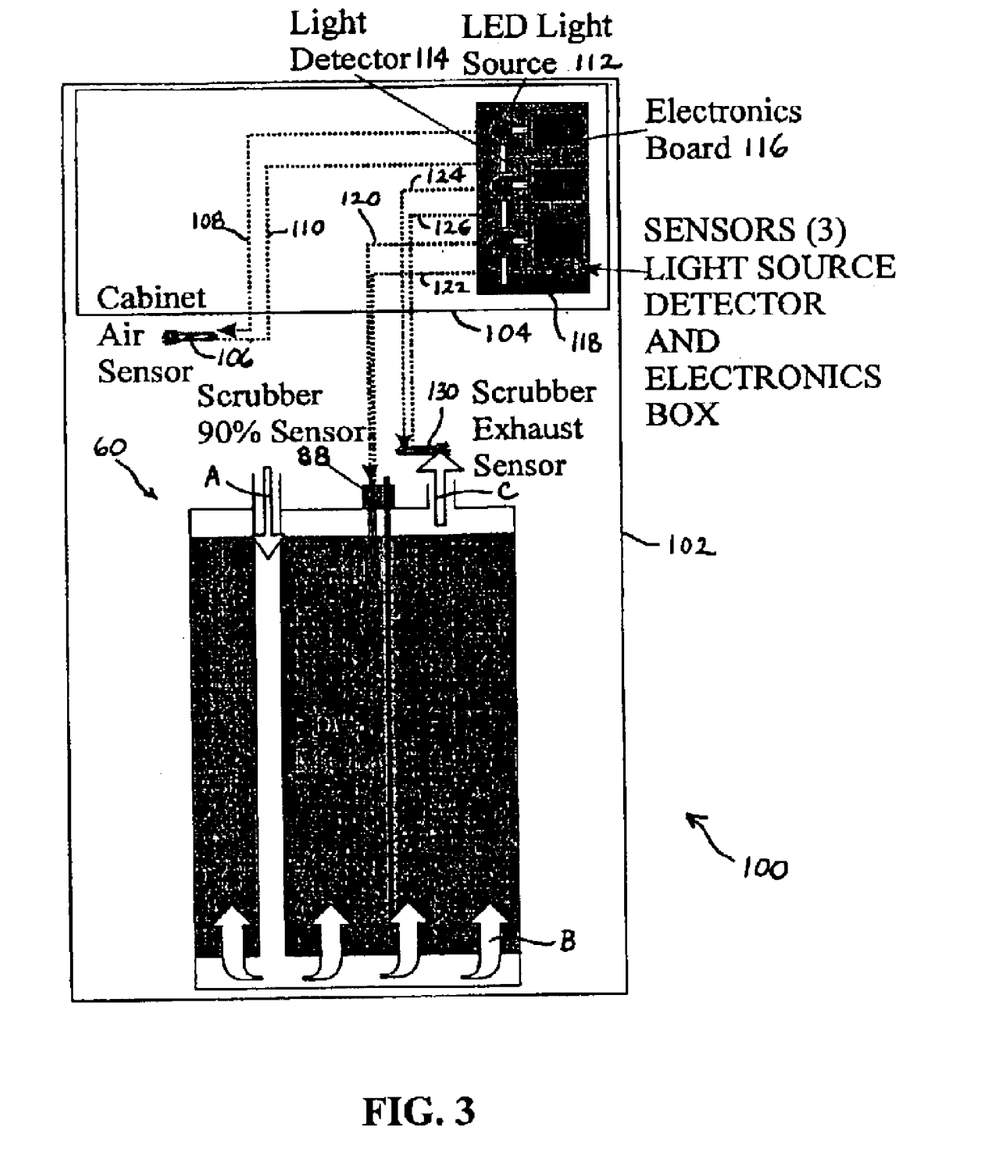
FIG. 3 is a schematic representation of a dry scrubbing unit for treatment of effluent gas from a semiconductor manufacturing tool, equipped with a gas-sensing assembly according to another aspect of the invention.

FIG. 3 is a schematic representation of a dry scrubbing system for treatment 100 of effluent gas from a semiconductor manufacturing tool, in which the system includes a gas-sensing assembly according to another aspect of the invention.

The dry scrubbing system 100 of FIG. 3 comprises a dry scrubbing unit 60 of the type illustrated and described with reference to FIG. 2 hereof. The scrubber unit 60 features a first gas sensor 88 of the type shown in FIG. 1, arranged for determination of 90% breakthrough of the contaminant species of the effluent stream, as previously described in connection with FIG. 2.

The dry scrubbing unit 60 is disposed in a gas cabinet 102 containing, in addition to the dry scrubber unit 60, a control module 104 including light source elements 112, detector elements 114, and electronics boards 116, as mounted in a box 118 of the module. The cabinet may be of a type having access doors, instrument panels associated with the control module 104 and vents or other air circulation structures whereby clean dry air can be flowed through the enclosed interior volume of the cabinet.

In the FIG. 3 system, a second gas sensor of the type shown in FIG. 1 is provided as scrubber exhaust sensor 130, to monitor the treated gas discharged from the dry scrubbing unit 60 for the presence of contaminant species (hydride and/or acid gas species) therein.

The FIG. 3 system also includes a third gas sensor of the type shown in FIG. 1, provided as a cabinet air sensor 106, to monitor the interior environment gas of the gas cabinet 102 for the presence of the contaminant hydride and/or acid gas species in such environment.

The FIG. 3 system is arranged with the first gas sensor 88 coupled via source light optical fiber 120 and detector optical fiber 122 to the light source 112 and light detector 114, respectively, with such light source and light detector in turn being operatively coupled with electronics board 116 in box 118.

In like manner, scrubber exhaust sensor 130 is coupled by source light optical fiber 124 and detector optical fiber 126 with the light source and light detector components, which in turn are coupled with the associated electronic board 116 in box 118. Similarly, cabinet air sensor 106 is coupled via source light optical fiber 108 and detector optical fiber 110 with respective light source and detector components, which in turn are coupled with the associated electronics board 116 in box 118.

The electronics boards 116 are each coupled with respective light emitting diode (LED) light source elements 112 and light detector elements 114, and such electronics boards comprise appropriate electronic circuitry and components for actuating the light source and detection elements, for sensing of the respective environments in which the individual sensors 88, 130, and 106 are disposed.

The FIG. 3 system thus provides three-point sensing for comprehensive monitoring of the cabinet sub-environments for the presence of hydride and/or acid gas species of interest. The individual sensors in combination with associated electronics in the control module can be arranged to provide outputs of varied type, including (i) audible alarms indicative of hydride and/or acid gas breakthrough, (ii) visual output gauges, (iii) menu-driven displays on computer monitors operatively linked to the control module, (iv) printed reports of the monitoring operation and sensing events, etc., as will be readily understood and implementable by those of ordinary skill in the art, without undue experimentation, based on the disclosure herein.

It will be correspondingly apparent that the gas sensors of the present invention may be widely varied in structure and arrangement, with respect to specific applications and implementations thereof.

The advantages of the optical gas sensors of the present invention include the following:

(2) low cost compared to available alternative detectors;

(3) insensitivity of the detector to relative humidity conditions and changes of relative humidity;

(4) ability to eliminate cross-sensitivities of the sensing element by simple selection of specific color-change material for the sensor;

(5) ability to non-extractively sample a gaseous environment, thereby enhancing safety, with no requirement of returning sampled gas to the main gas stream of effluent;

(6) low cost of ownership, involving one-time use of the calorimetric sensing element and replacement thereof only when it calorimetrically changes in detecting the presence of the target hydride and/or acid gas species, i.e., no continuously replaced consumables are required;

(7) capability of ready reuse of the optical gas sensor, by simple change of calorimetric target gas species indicator material subsequent to a detection event;

(8) absence of moving parts, which makes the optical gas sensor less susceptible to failure and life-time and maintenance issues;

(9) high efficiency in light transfer by fiber optics; and (10) inherent safety, involving light as the only energy delivered to the sensing element.

While the invention has been described herein in reference to specific aspects, features and illustrative embodiments of the invention, it will be appreciated that the utility of the invention is not thus limited, but rather extends to and encompasses numerous other aspects, features and embodiments, as will readily suggest themselves to those of ordinary skill in the art, based on the disclosure herein. Accordingly, the claims hereafter set forth are intended to be correspondingly broadly construed, as including all such aspects, features and embodiments, within their spirit and scope.

What is claimed is:

1. A gas sensor for detection of hydride and/or acid gas species, said gas sensor comprising:

(a) an elongated sensor body with a light-transmissive window affixed to a distal end portion thereof, said light-transmissive window defining a first side exterior to said elongated sensor body and a second side interior to said elongated sensor body;

(b) a sensing element mounted on the sensor body at the first, exterior side of the light-transmissive window and arranged for contact with gas susceptible to presence of said hydride and/or acid gas species therein, said sensing element changing color in contact with gas containing said hydride and/or acid gas species;

(c) a source light optical fiber mounted in the sensor body at the second, interior side of the light-transmissive window, to conduct source light to the sensing element through said light-transmissive window;

(d) a detector optical fiber mounted in the sensor body at the second, interior side of the light-transmissive window, to receive reflected source light from the sensing element through said light-transmissive window;

(e) a light source coupled to the source light optical fiber for supplying source light thereto; and (f) a detector coupled to the detector optical fiber and arranged to receive reflected source light from the detector optical fiber and to responsively produce an output indicative of presence or absence of hydride and/or acid gas species in gas contacted with said sensing element.

2. The gas sensor of claim 1, wherein the sensor body comprises a particulates-occluding member protectively arranged to suppress contact of the sensing element with particulates during contact of the sensing element with gas.

3. The gas sensor of claim 2, wherein the particulates-occluding member comprises a gas-permeable element overlying the sensing element.

4. The gas sensor of claim 3, wherein said gas-permeable element comprises an element selected from the group consisting of screens, meshes, grids, and non-woven webs.

5. The gas sensor of claim 2, wherein said gas-permeable element is arranged in spaced relationship to the sensing element.

6. The gas sensor of claim 1, wherein the sensing element comprises material selected from the group consisting of:

(I) hydride gas detection materials comprising a material selected from the group consisting of silver nitrate, metal hydroxides, metal carbonates, metal sulfates, mercury chloride ($HgCl_2$), gold ($Au^{+3}$) complexes, and color indicating dosimeter hydride detection materials; and (II) acid gas detection materials comprising a material selected from the group consisting of iron oxide and acid/base indicators.

7. The gas sensor of claim 1, wherein the sensing element comprises material selected from the group consisting of silver nitrate, metal hydroxides, metal carbonates, metal sulfates, mercury chloride ($HgCl_2$) and gold ($Au^{+3}$) complexes.

8. The gas sensor of claim 1, wherein the sensing element comprises material selected from the group consisting of iron oxide, methyl orange, bromocresol green, methyl red, bromocresol purple, bromothymol blue, and phenol red.

9. The gas sensor of claim 1, wherein the light source comprises a source selected from the group consisting of light emitting diodes, lasers, and filtered coherent light sources.

10. The gas sensor of claim 1, wherein the light source comprises a light emitting diode.

11. The gas sensor of claim 1, wherein the light source comprises a laser producing source light in the visible light spectrum.

12. The gas sensor of claim 1, wherein the light source comprises a laser producing source light in the UV spectrum.

13. The gas sensor of claim 1, wherein the light source comprises a laser producing source light in the IR spectrum.

14. The gas sensor of claim 1, wherein the detector comprises a photodiode.

15. The gas sensor of claim 1, wherein the detector comprises a photoresistor.

16. The gas sensor of claim 1, wherein the detector comprises comparator circuitry.

17. The gas sensor of claim 16, wherein the detector comprises comparator circuitry operatively coupled with the light source to provide a reference light source signal to said comparator circuitry.

18. The gas sensor of claim 1, wherein the sensing element changes color in contact with east one gas species selected from the group consisting of boranes, arsine, phosphine, silane, $F_2$, HF, HCl, chlorine, $ClF_3$, $SiF_4$, $Br_2$, HBr, HI, $BF_3$, $BCl_3$, and $H_nSiCl_{(a-4)}$ (wherein n=1 to 3, inclusive).

19. An effluent treatment system arranged to receive a gaseous effluent from a process generating same, said effluent treatment system comprising an effluent treatment unit constructed and arranged to remove hydride and/or acid gas species from the gaseous effluent to produce a treated gaseous effluent having reduced content of hydride and/or acid gas species, and at least one gas sensor as claimed in claim 1, arranged for detection of hydride and/or acid gas species in the gaseous effluent.

20. The effluent treatment system of claim 19, wherein the effluent treatment unit comprises a dry scrubber unit.

21. The effluent treatment system of claim 19, wherein said process comprises a semiconductor manufacturing process.

22. A gas sensor for detection of hydride and/or acid gas species, said gas sensor comprising:
(a) an elongated tubular sensor body having an open proximal end and an exteriorly threaded distal end portion, said distal end portion having interiorly disposed therein a fixturing member mounting a source light optical fiber and a detector optical fiber, and a light-transmissive window affixed thereto in distal spaced relation to the fixturing member;
(b) a sensing element mounted in distal relation to the light-transmissive window and arranged for contact with gas susceptible to presence of said hydride and/or acid gas species therein, said sensing element changing color in contact with an containing said hydride and/or acid gas species;
(c) a light source coupled to the source light optical fiber for impinging source light to the sensing element through the light-transmissive window; and
(d) a detector coupled to the detector optical fiber and arranged to receive reflected source light from the detector optical fiber and to responsively produce an output indicative of presence or absence of hydride and/or acid gas species in as contacted with said sensing element.

23. The gas sensor of claim 22, wherein the light-transmissive window comprises a material selected from the group consisting of glass, quart, fused silica, zinc selenide, zinc sulfide, sapphire, $CaF_2$, and $MgF_2$.

24. The gas sensor of claim 22, further comprising a particulates-occluding member protectively arranged to suppress contact of the sensing element with particulates during contact of the sensing element with gas.

25. The gas sensor of claim 24, wherein the particulates-occluding member comprises a protective mesh element.

26. The gas sensor of claim 25, wherein the protective mesh element is mounted on an open-ended retaining cap, at the end opening thereof, and the retaining cap is interiorly threaded, and threadably engaged with the exteriorly threaded distal end portion of the elongate tubular member.

27. The gas sensor of claim 26, wherein the protective mesh element is in spaced relationship to the light-transmissive window.

28. A gas sensor for detection of hydride and/or acid gas species, comprising: (1) an elongated sensor body with a light-transmissive window affixed to a distal end portion thereof, said light-transmissive window defining a first side exterior to said elongated sensor body and a second side interior to said elongated sensor body and having a color changing material at the first, exterior side, wherein said color changing material changes color in exposure to hydride and/or acid gas species, (2) an impinger at the second, interior side of the light-transmissive window for impinging radiation on the color changing material for reflection therefrom through the light-transmissive window, and (3) a receiver at the second, interior side of the light-transmissive window for receiving reflected radiation from the color changing material through the light-transmissive window and responsively generating an output upon a change of color of the color changing material indicative of a presence of hydride and/or acid gas species in gas contacting the color changing material.

29. The gas sensor of claim 28, wherein said gas sensor comprises an optical waveguide comprising said impinger and said receiver.

30. The gas sensor of claim 28, wherein said gas sensor comprises a control module comprising said impinger and said receiver.

31. The gas sensor of claim 30, wherein the control module produces an output selected from the group consisting of audible outputs, visual outputs, and combinations thereof.

32. The gas sensor of claim 30, wherein said impinger comprises a light source, said receiver comprises a light detector, and wherein said control module further comprises associated electronic circuitry for said light source and said light detector.

33. The gas sensor of claim 30, wherein the control module comprises a source light optical fiber and a detector optical fiber.

34. The gas sensor of claim 33, wherein the source light optical fiber impinges radiation on the color changing material for reflection therefrom.

35. The gas sensor of claim 33, wherein the detector optical fiber receives reflected radiation from the color changing material.

36. The gas sensor of claim 28, further comprising a gas-permeable protective member arranged to shield the color changing material from particulate contamination.

37. An effluent treatment system arranged to receive a gaseous effluent from a process generating same, said effluent treatment system comprising an effluent treatment unit constructed and arranged to remove hydride and/or acid gas species from the gaseous effluent to produce a treated gaseous effluent having reduced content of hydride and/or acid gas species, and at least one gas sensor as claimed in claim 28, arranged for detection of hydride and/or acid gas species in the gaseous effluent.

38. The effluent treatment system of claim 33, wherein the effluent treatment unit comprises a dry scrubber unit.

39. The effluent treatment system of claim 33, wherein said process comprises a semiconductor manufacturing process.

40. The gas sensor of claim 28, having no moving parts.

41. The gas sensor of claim 28, wherein the color changing material is isolated from the impinger and the receiver by the light-transmissive window.

42. The gas sensor of claim 30, wherein the light detector comprises a detector selected from the group consisting of a photodiode and a photoresistor.

43. The gas sensor of claim 30, wherein the light source comprises a source selected from the group consisting of a light emitting diode and a laser.

44. A method of detecting hydride and/or acid gas species in a gaseous medium latently susceptible to presence of same, said method comprising providing an elongated sensor body with a light-transmissive window affixed to a distal end portion thereof, said light-transmissive window defining a first side exterior to said elongated sensor body and a second side interior to said elongated sensor body and having a color changing material at the first side thereof that changes color in exposure to the hydride and/or acid gas species, contacting the gaseous medium with a color changing material at the first, exterior side of said light-transmissive window, while impinging on the color changing material an incident radiation from the second, interior side of the light-transmissive window, so that such incident radiation transmits through said window to the color changing material and is reflected from said color changing material, and monitoring the reflected radiation from the color changing material through said light-transmissive window to detect a change of the reflected radiation indicative of a change of color of the color changing material due to presence of hydride and/or acid gas species in said gaseous medium, thereby detecting the hydride and/or acid gas species in the gaseous medium.

45. The method of claim 38, further comprising generating an output from said monitoring upon detection of a change of the reflected radiation.

46. The method of claim 39, wherein the output comprises an alarm.

47. The method of claim 39, wherein the output comprises an audible output.

48. The method of claim 39, wherein the output comprises a visual output.

49. The method of claim 39, wherein the output comprises an audible and visible output.

50. The method of claim 38, wherein the color changing material comprises a material selected from the group consisting of:
(I) hydride gas detection materials comprising a material selected from the group consisting of silver nitrate, metal hydroxides, metal carbonates, metal sulfates, mercury chloride ($HgCl_2$), gold ($Au^{+3}$) complexes, and color indicating dosimeter hydride detection materials; and
(II) acid gas detection materials comprising material selected from the group consisting of iron oxide and acid/base indicators.

51. The method of claim 38, wherein the color changing material comprises a material selected from the group consisting of silver nitrate, metal hydroxides, metal carbonates, metal sulfates, mercury chloride ($HgCl_2$) and gold ($Au^{+3}$) complexes.

52. The method of claim 38, wherein the color changing material comprises a material selected from the group consisting of iron oxide, methyl orange, bromocresol green, methyl red, bromocresol purple, bromothymal blue, and phenol red.

53. The method of claim 38, wherein the gaseous medium comprises an effluent from a semiconductor manufacturing operation.

54. The method of claim 47, wherein the hydride and/or acid gas species comprises at least one species selected from the group consisting of boranes, arsine, phosphine, silane, $F_2$, HF, HCl, chlorine, Br2, $ClF_3$, $SiF_4$, $Br_2$, HBr, HI, $BF_3$, $BCl_3$, and $H_nSiCl_{(n-4)}$ (wherein n=1 to 3, inclusive).

55. The method of claim 48, wherein the color changing material is positioned to contact gaseous medium in a discharge end portion of a dry scrubber bed.

56. The method of claim 48, wherein the color changing material is positioned to contact gaseous medium discharged from a scrubber unit.

57. The method of claim 48, wherein the color changing material is positioned to contact gaseous medium in a gas cabinet.

58. The method of claim 38, wherein the color changing material is positioned to detect breakthrough of hydride and/or acid gas species in a sorbent bed.

* * * * *